US00PP17167P2

(12) United States Plant Patent
Bradford

(10) Patent No.: US PP17,167 P2
(45) Date of Patent: Oct. 24, 2006

(54) NECTARINE TREE NAMED 'LATE BRIGHT'

(50) Latin Name: *Prunus persica*
Varietal Denomination: LATE BRIGHT

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 2 days.

(21) Appl. No.: 11/311,174

(22) Filed: Dec. 20, 2005

(51) Int. Cl.
*A01H 5/00* (2006.01)

(52) U.S. Cl. ..... Plt./190
(58) Field of Classification Search ..... Plt./190
See application file for complete search history.

(56) References Cited
U.S. PATENT DOCUMENTS

PP5,664 P 2/1986 Bradford

*Primary Examiner*—Kent Bell
*Assistant Examiner*—Annette H Para

(57) ABSTRACT

The present invention relates to a nectarine tree, *Prunus persica*, and more particularly to a new and distinct variety broadly characterized by a large size, vigorous, hardy, self-fertile, productive and regular bearing tree. The fruit matures under the ecological conditions described in early to mid September, with first picking on Sep. 7, 2005. The fruit is very large in size, acidic and sweet in flavor, globose in shape, clingstone in type, firm in texture, yellow with red bleeding in flesh color, and about fifty percent red in skin color. The variety was developed as a first generation cross using 'September Red' (U.S. Plant Pat. No. 5,664) nectarine as the selected seed parent and an unnamed nectarine (unpatented) as the selected pollen parent.

1 Drawing Sheet

Latin name: *Prunus persica.*
Varietal denomination: 'LATE BRIGHT'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'LATE BRIGHT'. The present variety was hybridized by me in 1998, grown as a seedling on its own root in my greenhouse, and transplanted to a cultivated area of my experimental orchard at Bradford Farms near Le Grand, Calif. in Merced County (San Joaquin Valley).

The variety was developed as a first generation cross using 'September Red' (U.S. Plant Pat. No. 5,664) nectarine as the selected seed parent and an unnamed nectarine (unpatented) as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to its selected seed parent, 'September Red' (U.S. Plant Pat. No. 5,664) nectarine by producing late maturing clingstone nectarines that are red and yellow in skin color, yellow with red bleeding in flesh color, acidic and sweet in flavor, and nearly globose in shape but is distinguished therefrom by having a sweet instead of bitter kernel and by producing nectarines that are much larger in size.

SUMMARY OF VARIETY

In summary, the present variety is characterized by a large size, vigorous, hardy, self-fertile, productive and regular bearing tree. The fruit matures under the ecological conditions described in early to mid September, with first picking on Sep. 7, 2005. The fruit is very large in size, acidic and sweet in flavor, globose in shape, clingstone in type, firm in texture, yellow with red bleeding in flesh color, and about fifty percent red in skin color.

DRAWING

The accompanying photograph consists of four whole fruits positioned to exhibit the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Sep. 10, 2005, on the first multiplied tree on Nemaguard (unpatented) rootstock during its fourth growing season. All major color code designations are by reference to the Inter-Society Color Council, National Bureau of Standards. Common color names are also used occasionally.

Tree

Size: Large, reaching a height of 14' [4.27 m.] and a spread of 10' [3.05 m.] after four growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 700 hours.

Trunk:

*Size.*—Medium, with a maximum diameter of 3¾" [95.3 mm.] after the fourth growing season.

*Texture.*—Shaggy.

*Bark color.*—A Dark yellowish brown [78. d.yBr] and Deep brown [56. deep Br] variegation.

*Lenticels.*—Approximate Number Per Square Inch: 10.

*Color.*—Strong yellowish brown [74. s.yBr].

*Typical size.*—3/16" [4.8 mm.] to ⅜" [9.5 mm.].

*Shape.*—Eye-shaped to elongated.

Branches:

*Size.*—Diameter of limb is 1¾"[45 mm.] measured 12" above the crotch, 1⅛" [29 mm.] measured 12" above the first fork.

*Texture.*—Smooth on first year wood, increasing roughness with age.

*Color.*—1st Year Wood Topside: Grayish red [19. gy.R]. 1st Year Wood Underside: Brilliant yellow green [116. brill.YG]. Older Wood: Moderate yellowish brown [77. m.yBr].

*Lenticels.*—Number Per Square Inch: More than 40 on second year wood. Color: Light yellowish brown [76. l.yBr]. Typical size: 1/32" [0.8 mm.] to ⅛" [3.2 mm.]. Shape: Eye-shaped to elongated.

Leaves:

*Size.*—Medium. Average Length: 5⅝" [143 mm.]. Average Width: 1¾" [45 mm.].

*Arrangement.*—Alternate.

*Thickness.*—Medium.

*Form.*—Elliptical.

*Apex.*—Acuminate.

*Base.*—Acute with a base angle of 75 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Pale yellow green [121. p.YG].

*Petiole.*—Average Length: ½" [12.7 mm.]. Average Thickness: 1/16" [1.6 mm.]. Color: Light yellow green [119. l.YG].

*Stipules.*—Number: 2 per leaf, up to 6 per growing tip. Average Length: ¼" [6.4 mm.]. Color: Brilliant yellow green [116. brill.YG] becoming Dark yellowish brown [78. d.yBr] with maturity.

*Glands.*—Number: Usually 2, up to 6. Position: Both alternately and oppositely positioned on the petiole and base of blade. Size: Medium. Form: Reniform. Color: Brilliant yellow green [116. brill.YG] on the outside with a Dark brown [59. d.Br] center.

*Leaf buds.*—Pointed, medium in size.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Deep purplish pink [248. deep pPk].

Flowers: Perfect, complete, perigynous, usually a single pistil, typically thirty or more stamens, five sepals and petal locations alternately positioned.

*Type.*—Showy, large.

*Average flower diameter.*—1¾" [44.5 mm.].

*Number of petals.*—Usually five, with extra petal fragments rarely observed.

*Petal shape.*—Circular to oval.

*Petal margin.*—Somewhat wavy.

*Average petal diameter.*—11/16" [17.5 mm.].

*Average petal length.*—¾" [19.1 mm.].

*Petal apex.*—Rounded.

*Petal base.*—Rounded.

*Petal color.*—Pale pink [7. p.Pk] toward the apex, Light purplish pink [249. l.pPk] toward the base.

*Anther color.*—Strong reddish orange [35. s.rO] over Light yellow [86. l.Y] centers at bloom onset.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*—11/16" [17.5 mm.].

*Average stamen length.*—⅝" [15.9 mm.].

*Fragrance.*—Moderate.

*Blooming period.*—Medium to late compared with other varieties.

*Onset of bloom.*—One percent on Feb. 24, 2005.

*Date of full bloom.*—Mar. 5, 2005.

*Duration of bloom.*—One to two weeks, dependent on ambient temperature.

*Number per cluster.*—1 to 3 with single flowers most common.

FRUIT

Maturity when described: Firm ripe, Sep. 10, 2005.

Date of first picking: Sep. 5, 2005.

Date of last picking: Sep. 14, 2005.

Size: Uniform, very large.

*Average diameter axially.*—3 3/16" [81.0 mm.].

*Average diameter across cheek plane.*—3 1/16" [77.8 mm.].

*Average diameter across suture plane.*—2 15/16" [74.6 mm.].

*Typical weight.*—9.4 ounces [267 grams].

Form: Globose, uniform.

*Longitudinal section form.*—Circular to slightly oval.

*Transverse section through diameter.*—Circular to elliptical.

Suture: Extends from the stem to well beyond the pistil point, a sharp groove near the stem, a rounded groove along the side, a sharp groove near the apex.

Ventral surface: Rounded, lipped throughout on both sides, stronger toward the apex and stronger on one side.

Lips: Unequal along the side, fairly equal at the apex.

Cavity: Flaring, elongated in the suture plane, suture showing on both sides, Brilliant yellow [83. brill.Y] stem markings typical.

*Depth.*—5/8" [15.9 mm.].
*Breadth.*—1 1/8" [28.6 mm.].
Base: Slightly truncate, somewhat cordate if viewed parallel to the suture.
Apex: Rounded, but slightly cordate if viewed parallel to the suture.
Pistil point: Oblique, negligible in length, depressed within the suture.
Stem: Medium.
*Average length.*—7/16" [11.1 mm.].
*Average width.*—3/16" [4.8 mm.].
Skin:
*Thickness.*—Medium.
*Surface.*—Smooth.
*Tenacity.*—Tenacious to flesh.
*Astringency.*—Astringent.
*Tendency to crack.*—None observed in dry season.
*Color.*—Very deep red [14. v.deep R] sparsely streaked into a Dark reddish orange [38. d.rO] primary color over a Vivid yellow [82. v.Y] background.
Flesh:
*Color.*—Brilliant Yellow [83. brill.Y] with Moderate red [15. m.R] bleeding emanating outward from the stone.
*Surface of pit cavity.*—Very deep red [14. v.deep R] fibers breaking when twisted from the stone.
*Amygdalin.*—Abundant.
*Juice.*—Abundant, rich.
*Texture.*—Very firm, crisp.
*Fibers.*—Abundant, fine, tough.
*Ripens.*—Fairly even.
*Flavor.*—Sweet and acidic, typically 13 brix.
*Aroma.*—Slight.
*Eating quality.*—Very good.

STONE

Type: Clingstone.
Form: Oval.
Hilum: Narrow, oblong.
Base: Straight.
Apex: Obtuse, with an average tip angle of 105 degrees and a length of 1/8" [3.2 mm.].
Sides: Slightly unequal.
Surface: Irregularly furrowed and ridged toward the apex, pitted toward the base.
Ridges: Jagged.
External color: Dark yellowish brown [78. d.yBr].
Pit wall color when cracked: Deep yellowish brown [75. d.yBr].
Cavity surface color: Strong yellowish brown [74. s.yBr].
Average pit wall thickness: 1/4" [6.4 mm.].
Average width: 1" [25.4 mm.].
Average length: 1 9/16" [39.7 mm.].
Average breadth: 3/4" [19.1 mm.].
Tendency to split: Slight.
Kernel:
*Form.*—Oval.
*Skin color.*—Strong brown [55. s.Br] when dried.
*Pellicle color.*—Dark yellowish brown [78. d.yBr].
*Vein color.*—Dark yellowish brown [78. d.yBr].
*Taste.*—Sweet.
*Viable.*—Yes.
*Average width.*—1/2" [12.7 mm.].
*Average length.*—7/8" [22.2 mm.].
*Amygdalin.*—Scant.

USE

Market: Fresh market and long distance shipping.
Keeping quality: Good. Fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected seed parent, 'September Red' (U.S. Plant Pat. No. 5,664) nectarine by producing late maturing clingstone nectarines that are red and yellow in skin color, yellow with red bleeding in flesh color, acidic and sweet in flavor, and nearly globose in shape but is distinguished therefrom by having a sweet instead of bitter kernel and by producing nectarines that are much larger in size.

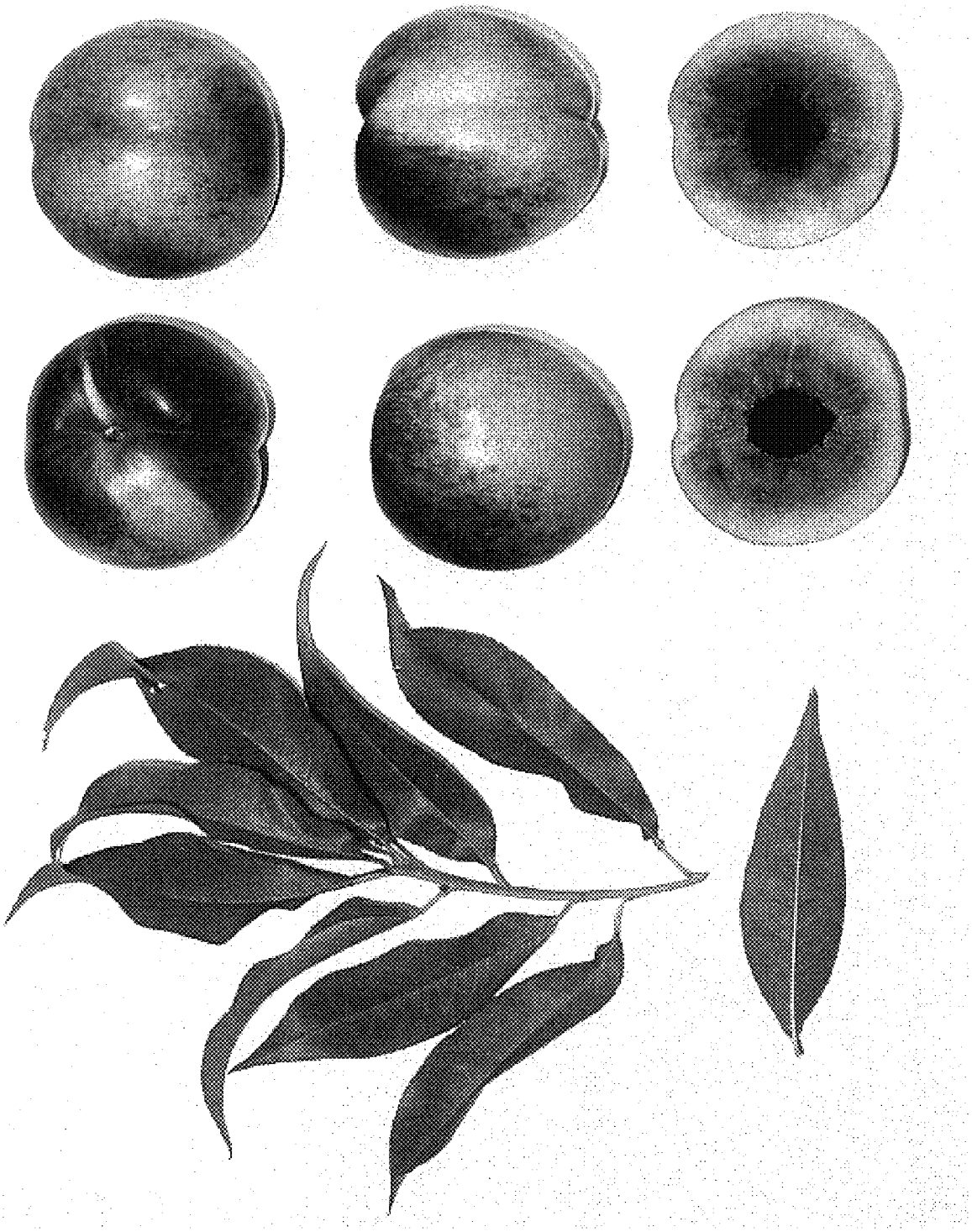

* * * * *